US 8,260,023 B2

(12) United States Patent
Thomsen et al.

(10) Patent No.: US 8,260,023 B2
(45) Date of Patent: Sep. 4, 2012

(54) FORWARD PROJECTION FOR THE GENERATION OF COMPUTED TOMOGRAPHY IMAGES AT ARBITRARY SPECTRA

(75) Inventors: Brian Thomsen, Milwaukee, WI (US); Xiaoye Wu, Rexford, NY (US)

(73) Assignee: General Electric Company, Schenectady, NY (US)

( * ) Notice: Subject to any disclaimer, the term of this patent is extended or adjusted under 35 U.S.C. 154(b) by 907 days.

(21) Appl. No.: 12/324,008

(22) Filed: Nov. 26, 2008

(65) Prior Publication Data
US 2010/0128948 A1    May 27, 2010

(51) Int. Cl.
*G06K 9/00* (2006.01)
(52) U.S. Cl. .......................... 382/131; 382/128
(58) Field of Classification Search .............. 382/131, 382/128
See application file for complete search history.

(56) References Cited

U.S. PATENT DOCUMENTS

| 2004/0028181 | A1* | 2/2004 | Charles, Jr. et al. | 378/92 |
| 2004/0264627 | A1* | 12/2004 | Besson | 378/5 |
| 2005/0084069 | A1* | 4/2005 | Du et al. | 378/98.9 |
| 2005/0259781 | A1* | 11/2005 | Ying et al. | 378/5 |
| 2006/0109950 | A1* | 5/2006 | Arenson et al. | 378/4 |
| 2008/0310598 | A1* | 12/2008 | Zhang et al. | 378/207 |

* cited by examiner

*Primary Examiner* — William C Dowling
*Assistant Examiner* — Ryan Howard
(74) *Attorney, Agent, or Firm* — McAndrews, Held & Malloy, Ltd.; Rick Wascher

(57) ABSTRACT

The present technology relates to the generation of a CT image under an arbitrary energy spectrum based on the results of a dual energy scan. In certain embodiments, a dual energy scan is conducted of an object and material basis decomposition is used to decompose the scanned object into two basis materials with known attenuation properties resulting in material density images. Along with knowledge of other imaging system information, forward projection is done under an arbitrary kV spectrum to generate an image as if the scanned object was scanned under this different kV spectrum. This prevents users from conducting unnecessary additional scans.

19 Claims, 2 Drawing Sheets

FORWARD PROJECTION FOR THE GENERATION OF COMPUTED TOMOGRAPHY IMAGES AT ARBITRARY SPECTRA

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present technology generally relates to the generation of digital images. More specifically, the technology relates to the use of forward projection to generate a computed tomography (CT) image under arbitrary tube spectra by a dual energy scan.

Dual energy imaging essentially involves taking multiple scans of the same target under the same conditions at two energy spectra. In a Dual Energy system, multiple scans are performed at the different energy levels (or energy spectra), and are used to identify different materials. For example, soft tissue and other lower density elements tend to attenuate x-rays to a lesser degree than bone and iodine contrast agent. Thus, performing two imaging scans, one at a higher tube voltage level (for example, 110-150 kVp), and another at a lower level (for example, 60-80 kVp) will provide more information about the materials being scanned than a conventional CT scan.

Dual energy projection data can be used to reconstruct images using basis material decomposition (BMD) algorithms. The generated images are representative of a pair of selected basis material densities. In addition to material density images, dual energy projection data can be used to produce a new image with X-ray attenuation coefficients equivalent to a chosen monochromatic energy. Such a monochromatic image includes an image where the intensity values of the voxels are assigned as if a CT image were created by collecting projection data from the subject with a monochromatic X-ray beam.

In the medical imaging field, dual energy CT scans are frequently performed at a low energy level of around 80 kVp, and at a high energy level of around 140 kVp. From the images obtained during these scans, it becomes possible to generate basis material density images and monochromatic images (i.e., images that represent the effect of performing a computed tomography scan with an ideal monochromatic tube source). Given a pair of material density images, it is possible to generate other basis material image pairs. For example, from a water and iodine image of the same anatomy, it is possible to generate a different pair of material density images such as calcium and gadolinium. Similarly, from a pair of basis material images, it is possible to generate a pair of monochromatic images, each at a specific energy. The inverse is also possible, i.e. from a pair of monochromatic images, a pair of basis material image pairs can be derived, or a pair of monochromatic images at different energies.

Occasionally, however, it can be helpful to also generate images as if the patient were scanned using another tube spectra without actually having to do the additional scan. For example, in certain instances it might aid a radiologist to view an imaged object at a conventional energy level of 120 kVp. Typically, this would require an additional scan to be performed at the desired energy level. This is a time-consuming step that can further expose a patient to undesired levels of radiation. Further, because time will have elapsed since the initial imaging procedure and circumstances will have changed, it will be impossible to capture the image exactly as it was obtained in the original dual energy CT scan.

As a result, there exists a need for generating an image result as if a CT scan was performed at an arbitrary energy level or spectra, using the imaging results obtained from a dual energy scan.

BRIEF SUMMARY OF THE INVENTION

Material decomposition is conducted to obtain material property factors based on the dual energy scan. For example, the dual energy scan is decomposed an into material basis pairs representing material densities. That is, the attenuation values of the materials in the imaged object are determined for each of the dual energy scans. For example, using the attenuation of a material (for example, bone) at a first energy level scan and the attenuation of the material at the second energy level scan, the linear attenuation coefficient for that material can be obtained such that the attenuation value for that material can be calculated for any energy level. In certain embodiments, linear attenuation properties can be a linear attenuation coefficient, for example.

Next, the basis material density images, for example, where the basis materials are water and iodine, are used to forward project at an arbitrary energy spectrum based upon the material densities, the material attenuation coefficients and known properties of the imaging system. For example, after identifying the linear attenuation properties of a material located at a location having a coordinate (x, y), the attenuation value for that material at that location can be generated by plugging in the energy levels comprising an arbitrary energy spectrum into an equation, such that the attenuation value for that material can be generated.

Certain embodiments also provide techniques whereby the determination of the CT projections obtained under an arbitrary tube spectra is done completely in projection space without ever generating material density images or monochromatic images.

DETAILED DESCRIPTION OF THE INVENTION

The present technology describes systems and methods for using forward projection techniques, or basis material projection techniques to synthesize CT images at an arbitrary energy spectra using material density images obtained during dual energy imaging, and known material properties.

Using dual energy imaging, it is possible to reconstruct material density images based on the information obtained from two separate scans, taken at different energy levels. For example, a CT scan taken at a lower energy level will yield different results than a scan taken at a higher energy level, based on the materials properties of the materials in the scan. Materials in the scanned object will attenuate the X-rays in the low energy scan more than they will attenuate X-rays in the high energy scan. Additionally, at a given energy level, denser materials will attenuate X-rays more than less dense materials. Therefore, dual energy CT scanning can be used to identify material densities in an image, which can be decomposed into two basis material images such as water and iodine, calcium and iodine, or water and calcium, for example.

The present technology presents systems and methods to use data obtained during a dual energy scan to generate a synthesized image at an arbitrary energy spectra. In other words, the present technology provides for the generation of an image at a third energy spectra, without conducting a scan at the third energy level. For example, in certain embodiments, after conducting a dual energy scan at energy levels of 80 and 140 kVp, respectively, the present technology provides systems and methods for the generation of an image as it would look if taken at an energy level of 120 kVp, 50 kVP, 200 kVp, or any other arbitrary level. This can help to produce images that a user most prefers, or is most comfortable with reading.

Figure 1:
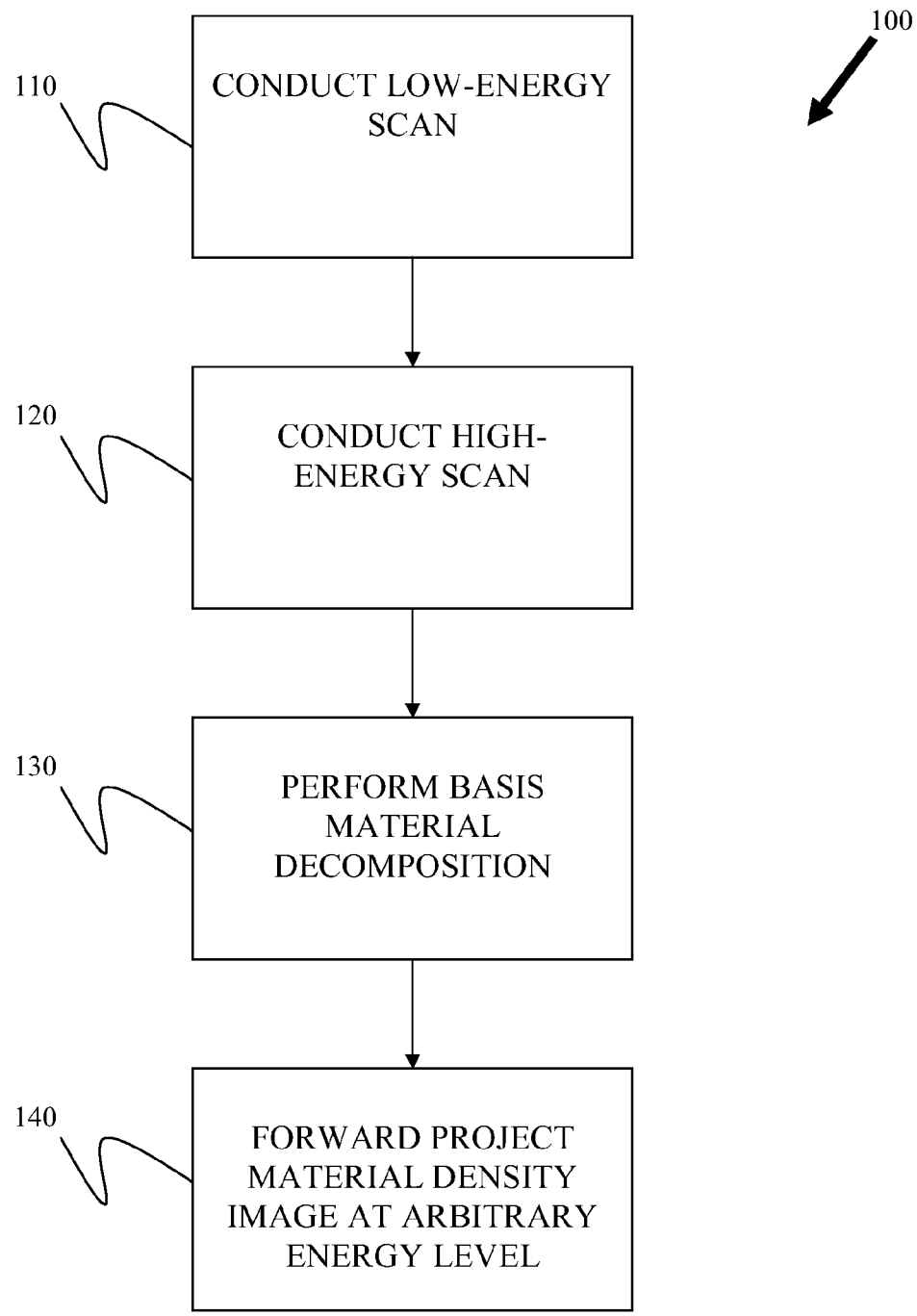
FIG. 1 depicts a flow diagram of a method in accordance with certain embodiments of the present technology.

FIG. 1 is a flow diagram for a method 100 practiced in accordance with an embodiment of the present technology. In step 110, a user such as a radiologist or other medical practitioner, conducts a low-energy scan. For example, the user may conduct a low-energy scan at 80 kVp. In certain embodiments, a material density image is generated based on the results of the low-energy scan. In other embodiments, the information from the scan is taken without generating an image.

In step 120, the user conducts a high-energy scan. For example, the user may conduct a CT scan at 140 kVp. Though it is stated here for reference purposes that the low-energy scan is conducted first, the present technology is not limited to a particular order for dual energy scans. In certain embodiments, the low and high energy scans can be conducted simultaneously using separate X-ray imaging tubes or through an interleaved acquisition. Alternatively, in certain embodiments, the high-energy scan may be conducted before the low-energy scan. It is also not significant, for purposes of the present technology, that the low energy scan be conducted within a particular energy range, or at an energy spectrum. Nor is it significant that the high energy scan be conducted within a particular energy range. For example, the low-energy scan may be conducted at 20 kVp, 80 kVp, 120 kVp, or 200 kVp and the high-energy scan may be conducted at 50 kVp, 120 kVp, or 140 kVp. The use of the terms "high" and "low" are used merely to distinguish the two scans from each other, and not assign a predetermined energy level to the scan. Thus, the low-energy scan is the scan conducted at the lower energy level of the two scans, no matter how high the energy levels may be. As with step 110, in certain embodiments, a material density image can generated based on the results of the high-energy scan; however, other embodiments will extract the information from the scan without generating an image.

In step 130 basis material decomposition is performed. The information in the dual energy scan can be used to decompose the scanned object into two material density images such that material densities can be obtained. In certain embodiments, the material density projections can be obtained without the generation of images, for example. Basis material decomposition in projection space processing of dual energy CT scans allows for the decomposition of the target into material basis pairs that represent the material density line integration. In other words, the data obtained from the dual energy scans can be broken down based on the attenuation values and known properties about the identified materials to obtain linear attenuation properties of the scanned object. The linear attenuation properties can be used to determine the attenuation values of the materials at any energy level, even those that were not used in the dual energy scan. For example, the attenuation value provided by a material has at a detector for a scan taken at a first energy level and a second energy level can be used to compute what the attenuation value will be at that detector for the material when scanned at any energy level.

Additionally, factors affecting the imaging process are obtained and broken down during the basis material decomposition step so that all materials in the imaged object can be represented by an equation that considers the factors. In certain embodiments, factors considered in the basis material decomposition step 130 can include technical factors of the imaging scan routines, for example energy levels, imaging detector properties and scan angles.

In certain embodiments it may be helpful or even necessary to obtain the attenuation affects of the bowtie filter. The attenuation affects of the bowtie filters may be dependent upon the detector pixel position, and the energy level recorded. Further, the basis material decomposition process can identify energy dependent linear attenuation properties, or linear attenuation coefficients of the object being scanned.

Additional factors determined in certain embodiments of step 130 of method 100 include, but are not limited to: the projection level at a particular detector and a particular gantry angle; the corrected projection received at a particular detector, and a particular gantry angle; and the correction coefficient at a particular detector.

In step 140, forward projection is done through the two material basis images obtained through material basis decomposition. Alternatively, basis material density projections of step 140 may be done in projection space by transforming the projections from the high and low kVp projections, through projection based material decomposition. Projection values are obtained for a particular energy spectrum of interest. For example, where a dual energy scan is conducted in steps 110 and 120 at energy levels of 80 kVp and 140 kVp, respectively, a CT image can be generated as if was scanned at 120 kVp at step 140, based upon the factors obtained during step 130.

In certain embodiments, where there are 2 identified materials, the forward projection of the image can be modeled according to the following equation:

$$p_i(\theta) = -\log\left[\frac{\int b(E,i) * S(E) * e^{-\int (m_1(x,y)\mu_1(E) + m_2(x,y)\mu_2(E))dl} dE}{\int S(E) * b(E,i) dE}\right]$$

Equation 1 where:
$m_1(x,y)$: density of material 1 at location coordinate x,y;
$m_2(x,y)$: density of material 2 at location coordinate x,y;
$b(E,i)$: the attenuation level provided by the bowtie filter at an energy level E, as received at detector i;
$\mu_1(E)$: the linear attenuation coefficient of material 1;
$\mu_2(E)$: the linear attenuation coefficient of material 2;
$p_i(\theta)$: projection at detector i at gantry angle $\theta$;
$\theta$: the angular difference between the rays that connect each detector element (i) and the tube source due to the arc shape of the detector;

$p_{c,i}(\theta)$: corrected projection at detector i at gantry angle $\theta$; and S(E): spectrum (or energy level) at which forward projections are computed (for example, at 120 kVp)

In certain embodiments, these projections will need to correct for the attenuation effects of various other materials in the image such as water or iodine, for example. However, calibration for water can cause problems because it would also create issues due to detector imperfections and beam hardening. Because detector imperfections are already accounted for in the generation of the material density images, certain embodiments of the present technology provide a method for applying a synthetic water scan that can be used with the projections obtained in equation 1 to provide an updated projection value. In certain embodiments, the coefficients for the synthetic spectrally corrected projections for beam hardening through water or soft tissue can be obtained by the following equation:

$$p_{c,i}(\theta)=p_i(\theta)*a_1(i)+p_i(\theta)^2*a_2(i)+p_i(\theta)^3*a_3(i) \quad \text{Equation 2}$$

where:

$a_x(i)$: correction coefficient x at detector i.

Thus, projections under a selected spectrum can be done through the material density images under an arbitrary energy spectrum, without having to perform the actual scan at the energy level in accordance with the steps of method 100, as depicted in FIG. 1. The presently described technology provides methods that can present an image that is representative of a conventional clinical CT scan at 120 kVp, or another arbitrary energy level.

As described, in certain embodiments of the present technology, the forward projection process may be conducted based upon material density or monochromatic images that have been previously generated from steps 110 and 120 of a previously conducted dual energy scan. In alternative embodiments, the forward projection generation process for a selected kVp spectrum can be done without the generation of the material density, or monochromatic images described. The forward projection process can be done in "projection space," with the knowledge obtained from the high energy and low energy scans. In other words, material density images, or monochromatic images based on the high energy and low energy scans of steps 110 and 120 of the method described above need not be actually generated for the forward projection step 140.

The ability to produce such images provides several benefits. It can be useful for users that are used to looking at images from a particular energy level. For example, certain practitioners may prefer, or be used to looking at CT images that were taken at 120 kVp; however, the dual energy scanning process used to take images may not provide a 120 kVp scan. By applying the techniques of the present technology, the user can have an image produced that is accurate for the energy level for which the user is most comfortable with.

The present technology also can highlight the benefits of monochromatic images, and drive acceptance. For example, by being able to generate a 120 kVp image, the present technology provides a user a basis for comparison. A user can then see how the monochromatic images compare with the 120 kVp image, which is the image that the user might normally be used to. Because monochromatic images are a relatively new image type in the field, the ability to see a comparison will make the differences evident and drive acceptance in the value of the monochromatic images.

The present technology can also be useful in phantom design. Clinical phantoms are typically designed with the intent of demonstrating a certain pathology in an artificial environment. Materials are identified that result in a desired CT number (matching the values seen in a clinical scenario) under a conventional scan (for example, 120 kVp). Dual energy can provide the ability to make known how the CT attenuation value depends on the energy level, thus it will be important to choose materials that behave the same across a range of energy levels, and to confirm that the attenuation values under arbitrary spectra (such as 120 kVp) are indeed as expected. The present technology also allows users to generate images at any spectrum that may be useful for a specific clinical need.

Figure 2:
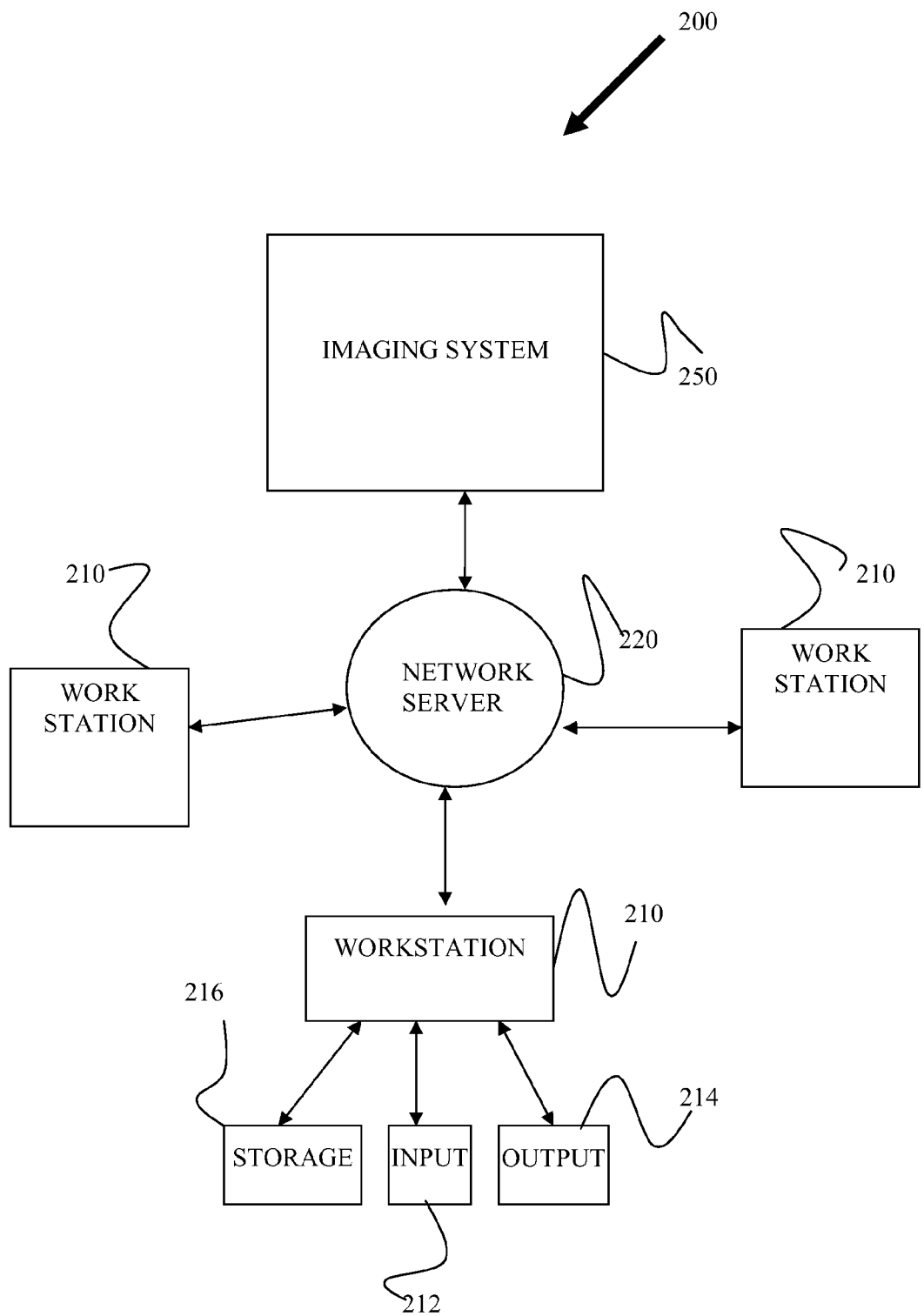
FIG. 2 depicts a diagram of a system for forward projecting material density images at arbitrary energy level in accordance with an embodiment of the present technology.

Certain embodiments also present a system for reconstructing material density images at arbitrary energy levels. FIG. 2 depicts one embodiment of a system 200 for reconstructing images in accordance with the present technology. An imaging system 250 is provided for scanning an object, for example, by performing a dual energy scan in accordance with the methods described herein. The imaging system 250 can be connected to a computer workstation 210 directly, or to a plurality of workstations 210 through a network server 220. The computer workstation 210 can take the data from performed imaging routines, for example, dual energy scans, and generate material density images at arbitrary energy levels by applying the methods of the present technology, for example. In certain embodiments, the computer workstation can display the images, and other items via a display or another output 214, for example. A user can interact with the workstation 210 via an input 212 such as a keyboard or mouse. In certain embodiments, the workstation 210 can have a storage, 216, such as a hard drive, database, or other form of memory capable of maintaining information. The workstation 210 has a processor that can take the data received from the imaging system 250 and, using the methods described herein generate a material density image at an energy level of the user's selection.

In certain embodiments, the workstation 210 may use information input from a user via the input 212 terminal, or from the system's storage. For example, the imaging system 250 may perform a dual energy scan of an object. The workstation processor may identify materials in the scanned object, for example, bone and soft tissue. The workstation may then obtain basis material information from the storage unit 216 and/or via the input 212 by a user. For example, the user may input the name of the patient that was imaged by the imaging system 250 via the input 212. The workstation can then reference a database in the storage unit 216 to obtain information about the density of the materials identified in the object. For example, there may be patient specific information, or general information about the materials identified in the storage unit 216. Alternatively, the user may input the material information via the input 212, and/or the workstation may generate the material information based upon the results of the dual energy scan, for example.

Via the processor in the workstation 210, the system can then automatically or at the instruction of the user perform the methods described herein to forward project the material density image based upon an arbitrary energy level which may be selected by the user, the results of the dual energy scan, and the other data obtained via the storage 216 or the input 212. The material density image can be displayed via the output 214, for example.

The present technology has now been described in such full, clear, concise and exact terms as to enable any person skilled in the art to which it pertains, to practice the same. It is to be understood that the foregoing describes preferred embodiments and examples of the present technology and that modifications may be made therein without departing from the spirit or scope of the invention as set forth in the claims. Moreover, while particular elements, embodiments and applications of the present technology have been shown and described, it will be understood, of course, that the present technology is not limited thereto since modifications can be made by those skilled in the art without departing from the scope of the present disclosure, particularly in light of the foregoing teachings and appended claims. Moreover, it is also understood that the embodiments shown in the drawings, if any, and as described above are merely for illustrative purposes and not intended to limit the scope of the invention, which is defined by the following claims as interpreted according to the principles of patent law, including the Doctrine of Equivalents. Further, all references cited herein are incorporated in their entirety.

The invention claimed is:

1. A method for reconstructing a computed tomography image of an object at an arbitrary energy spectrum, the method comprising the steps of:
   conducting a first computed tomography scan at a first energy spectrum;
   conducting a second computed tomography scan at a second energy spectrum;
   performing basis material decomposition to the first and second computed tomography scans to obtain linear attenuation properties for a first basis material and a second basis material;
   forward projecting new projection values at an arbitrary energy spectrum based upon:
      the linear attenuation properties of the first basis material and the second basis material; and
      the arbitrary energy spectrum; and
   reconstructing a synthesized material density image projected at the arbitrary energy level;
wherein the reconstruction of a synthesized material density image at an arbitrary energy spectrum is conducted in projection space without generating separate material density images based on the first energy spectrum and the second energy spectrum.

2. The method of claim 1, wherein the arbitrary energy spectrum is distinct from the first energy spectrum and the second energy spectrum.

3. The method of claim 1, wherein the first energy level is a low-energy level, and the second energy level is a high-energy level.

4. The method of claim 1, wherein the first energy level is 80 kVp.

5. The method of claim 4, wherein the second energy level is 140 kVp.

6. The method of claim 1, wherein at least one of the first or second materials is water.

7. The method of claim 1, wherein at least one of the first or second materials is iodine.

8. The method of claim 1, wherein at least one of the first or second materials is calcium.

9. The method of claim 1, further comprising the steps of generating at least one material density image or monochromatic image based upon the dual energy scan, wherein the linear attenuation properties of the basis materials are obtained from the at least one material density image or monochromatic image.

10. A method for determining the attenuation level of a first basis material and a second basis material at a detector for an arbitrary energy level based on a dual energy scan of an object, comprising using a computer to operate the following steps:
    decomposing the scanned object into a first basis material and a second basis material to determine the linear attenuation properties of the first basis material and the second basis material;
    generating a simulated attenuation level at the detector at a first object location for the arbitrary energy spectrum based on the linear attenuation properties of the first and second basis materials at the first object location, the density of the first and second basis materials, and the arbitrary energy spectrum;
    wherein the generation of a simulated attenuation level is conducted in projection space without generating separate material density images based on the dual energy scan.

11. The method of claim 10, further comprising the step of generating a simulated attenuation level at the detector at a second object location for the arbitrary energy spectrum based on the linear attenuation properties of the first and second basis materials at the second object location, the density of the first and second basis materials, and the arbitrary energy spectrum.

12. The method of claim 10, wherein at least one bowtie filter is used in the dual energy scan, further comprising the step of determining the material attenuation of the bowtie filter at the detector.

13. The method of claim 10, further comprising the step of correcting the simulated attenuation level at the detector for the first and second material at the first location by applying a synthetic water scan.

14. The method of claim 10, wherein the dual energy scan is conducted at a low-energy level of 80 kVp, and a high-energy level of 140 kVp.

15. The method of claim 14, wherein the arbitrary energy level is 120 kVp.

16. The method of claim 10, wherein the arbitrary energy level is a monochromatic energy level.

17. A method for generating a digital image of an object comprising the following steps:
    conducting a dual energy scan on an object;
    decomposing the scanned object into two basis materials, the basis materials having known linear attenuation properties;
    generating a simulated attenuation level at the detector at a plurality of locations on the dual energy scan for an arbitrary energy spectrum based upon the known linear attenuation properties of the basis materials and the arbitrary energy spectrum; and
    generating an image under an arbitrary energy spectrum based on the attenuation level generated for at least the first material and the second material at every location on the dual energy scan
    wherein the generation of a simulated attenuation level is conducted in projection space without generating separate material density images based on the dual energy scan.

18. The method of claim 17, wherein the arbitrary energy level is 120 kVP.

19. The method of claim 17, wherein the first and second materials are different and selected from the group consisting of water, calcium and iodine.

* * * * *